US006262061B1

(12) United States Patent
Sanchez et al.

(10) Patent No.: US 6,262,061 B1
(45) Date of Patent: Jul. 17, 2001

(54) TREATMENT OF PANIC ATTACKS

(75) Inventors: Connie Sanchez, Glostrup; Sandra Hogg, Frederiksberg, both of (DK); Maria Jessa, Warsawa (PL)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 09/685,016

(22) Filed: Oct. 6, 2000

Related U.S. Application Data

(63) Continuation of application No. PCT/DK99/00190, filed on Mar. 30, 1999.

(30) Foreign Application Priority Data

Apr. 7, 1998 (DK) .................................................. 0501/98

(51) Int. Cl.⁷ .................................................. A61K 31/505
(52) U.S. Cl. ............................................................ 514/278
(58) Field of Search ................................................ 514/278

(56) References Cited

FOREIGN PATENT DOCUMENTS

WO 92/22554    12/1992   (WO) .

OTHER PUBLICATIONS

G. Sanchez et al., "The Selective $\sigma_2$–Ligand Lu 28–179 Has Potent Anxiolytic–Like Effects in Rodents," *The Journal of Pharmacology and Experimental Therapeutics* 263, 3: 1323–1332 (1997).

*Primary Examiner*—Raymond Henley, III
(74) *Attorney, Agent, or Firm*—Darby & Darby

(57) ABSTRACT

The compound 1'-[4-[1-(4-fluorophenyl)-1H-indole-3-yl]-1-butyl]-spiro[isobenzo-furan-1(3H),4'-piperidine] is active in models predictive of effect on panic attacks and is useful for the preparation of a medicament for the treatment of diseases associated with panic attacks.

11 Claims, No Drawings

TREATMENT OF PANIC ATTACKS

This application is a continuation of PCT/DK99/00170 filed Mar. 30, 1999.

FIELD OF INVENTION

The present invention relates to the use of the compound 1'-[4-[1-(4-fluorophenyl)-1H-indole-3-yl]-1-butyl]-spiro[isobenzofuran-1(3H),4'-piperidine] or a pharmaceutically acceptable salt thereof for the preparation of medicaments for the treatment of panic attacks.

BACKGROUND OF THE INVENTION

International Patent Publication No. WO 92/22554 describes a series of sigma receptor ligands considered useful for the treatment of a range of psychic and neurological disorders. The structure activity relationship of these compounds has been further investigated by Perregaard, J. et al., *J. Med. Chem.*, 1995, 38, 11,p. 1998–2008.

Among other compounds, International Patent Publication No. WO 92/22554 discloses the compound 1'-[4-[1-(4-fluorophenyl)-1H-indole-3-yl]-1-butyl]-spiro[isobenzofuran-1(3H),4'-piperidine],

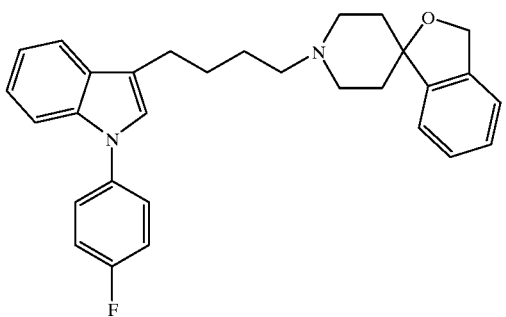

which is the subject of the present invention. This compound was shown in Perregaard, J. et al., *J. Med. Chem.*, 1995, 38, 11, p. 1998–2008 to be a potent and selective sigma ligand, in particular a sigma₁ ligand. Furthermore, the anxiolytic potential of the compound was tested in the black/white exploration test in rats, which is an animal model predictive for effect in the treatment of generalised anxiety disorder. It was found to be active over a large dose range. Results of further tests in generalised anxiety disorder models are reported in *J. Pharmacol Exp Ther.*, 1997, 283, No. 2.

Co-pending Danish patent application No. 0071/98 discloses the effect of the compound in the treatment of addiction to drugs and other substances of abuse.

Evidence has been presented from studies of the biology and function of sigma receptors that sigma receptor ligands may be useful in the treatment of a range of psychic and neurological disorders, including psychosis and movement disorders, such as dystonia and tardive dyskinesia, and motor disturbances associated with Huntington's chorea or Tourette's syndrome and in Parkinson's disease (Walker, J. M. et al. *Pharmacological Reviews*, 1990, 42, 355). The known sigma receptor ligand, rimcazole, clinically shows effects in the treatment of psychosis (Snyder, S. H., Largent, B. L. *J. Neuropsychiatry*, 1989, 1, 7) and a group of sigma receptor ligands have been described to show antihallucinogenic activity in animal models (International Patent Publication No. WO 9103243).

Sigma receptor ligands have also been reported to be involved in modulation of NMDA receptor mediated events in the brain and to act as anti-ischemic agents in in vivo tests (Rao, T. S. et al,. *Molecular Pharmacology*, 1990, 37, 978). In addition to ischemia, the sigma receptor ligands may also be useful in the treatment of other such NMDA receptor mediated events, e.g. epilepsy and convulsion.

Also, some sigma receptor ligands have been found to show anti-amnesic effects in an animal model (Early et al., *Brain Research*, 1991, 546, 281–286). Sigma ligands have been shown to influence central acetylcholine levels in animal models (Matsuno et al, *Brain Research*, 1992, 575, 315–319; Junien et al, *Eur. J. Pharm.*, 1991, 200, 343–345) and may, therefore, have potential in the treatment of senile dementia of the Alzheimer type.

Finally, some guanidine derivatives having sigma receptor activity have been disclosed to be useful as anxiolytics (International Patent Publication No. WO 9014067) and some sigma receptor ligands have been found to bind to the cocaine binding site on the dopamine transporter and others have been found to inhibit dopamine uptake (Izenwasser, S., et al, *Eur. J. Pharmacol.*, 243, 201–205 and Woodward, J. J. and Harms, J., *Eur. J. Pharmacol.*, 210, 265–270.

Diseases associated with panic attacks as a major element include panic disorder, specific phobias and agoraphobia. Specific phobias and agoraphobia both occur with or without panic attacks. According to DSM IV panic disorder, specific phobias and agoraphobia constitute distinct sub-classes of psychic illnesses and it is widely recognised that it is possible to differentiate these disorders from generalised anxiety disorder with respect to diagnostic, genetic (Kendler K. S. et al., *Arch Gen. Psychiatry.*, 1995, 52, 347–383) and pharmacological criteria.

Generalised anxiety disorder is treated with benzodiazepines such as diazepam and midazolam which are not employed in the treatment of panic and $5HT_{1A}$ receptor agonists such as buspirone which is reported to be ineffective in the treatment of panic (Fulton B. and Brogden R. N. Buspirone: *CNS Drugs*, 1997, 7(1), 68–88). The therapies of choice in panic and in other panic associated disorder include high potency benzodiazepines and compounds normally associated with the treatment of depression. Selective serotonin re-uptake inhibitors produce a significant reduction in the severity of the symptoms associated with panic and are better tolerated than the alternative treatments (Bertani A. et al., *Depression and Anxiety*, 1997, 4, 253; Sheehan and Harnett-Sheenan, *J.Clin.Psychiatry*, 1996, 57(suppl. 10), 51–60). As a result they are now becoming first choice treatments in panic disorder. The serotonin re-uptake inhibitors are not useful in the treatment of generalised anxiety disorder.

Studies have shown that patients suffering from panic attacks, in particular in association with agoraphobia, have a quality of life impairment comparable with or greater than the disability found in patients with alcoholism, schizophrenia or personality disorders. Furthermore the current treatments are not always effective or cause unacceptable side-effects.

Consequently, there is a need for alternative therapies useful in the treatment of disorders associated with panic attacks.

It has now, surprisingly, been found that the compound of the invention shows a beneficial effect in the treatment of panic attacks.

DESCRIPTION OF THE INVENTION

According to the present invention a novel use of 1'-[4-[1-(4-fluorophenyl)-1H-indole-3-yl]-1-butyl]-spiro[isobenzo-furan-1(3H),4'-piperidine], namely for the preparation of a medicament useful in the treatment panic attacks is provided.

The term treatment of panic attacks contemplates treatment of any disease which is associated with panic attacks including panic disorder, specific phobias, social phobia and agoraphobia in which panic attacks occur. These disorders are further defined in the DSM IV. A panic attack is a discrete period in which there is a sudden onset of intense apprehension, fearfulness or terror, often associated with feelings of impending doom. During the attack symptoms such as palpitations, sweating, trembling, sensations of shortness of breath, feeling of choking, chest pain or discomfort, nausea, feeling dizzy, feelings of unreality, fear of losing control or going crazy, fear of dying, paresthesias and chills or hot flushes are present.

Panic disorder is characterised by recurrent unexpected panic attacks about which there is a persistent concern. Agoraphobia is anxiety about, or avoidance of, places or situations from which escape might be difficult or in which help may not be available in the event of a panic attack. Specific phobia and social phobia (together formerly simple phobia) are characterised by marked and persistent fear that is excessive or unreasonable, cued by the presence or anticipation of a specific object or situation (flying, heights, animals, seeing blood etc.) or social performance situations.

The disorders in which panic attacks occur are differentiated from each other by the predictability of the occurrence of the attacks, for example, in panic disorder the attacks are unpredictable and not associated with any particular event, whereas in specific phobia the attacks are triggered by specific stimuli.

The phrase "treatment of panic disorder" means a reduction in the number or prevention of attacks and/or relief of the severity of the attacks.

According to the invention the compound 1'-[4-[1-(4-fluorophenyl)-1H-indole-3-yl]-1-butyl]-spiro[isobenzo-furan-1(3H),4'-piperidine] may be used as the base of the compound or as a pharmaceutically acceptable acid addition salt thereof or as an anhydrate or hydrate of such salt. The salts of the compound used in the invention are salts formed with non-toxic organic or inorganic acids. Exemplary of such organic salts are those with maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic and theophylline acetic acids, as well as the 8-halotheophyllines, for example 8-bromo-theophylline. Exemplary of such inorganic salts are those with hydrochloric, hydrobromic, sulfuric, sulfamic, phosphoric and nitric acids. Preferably the compound is used as the base or the fumarate.

The compounds used in the method of the invention have been found to inhibit the defensive running in a model of ultrasound-induced defensive behaviour in Lister hooded rats which is a test model for panic attacks and effects of potential antipanic drugs. (Beckett et al., *Psychopharmacol.*, 1996, 127, 384–390).

According to the invention, 1'-[4-[1-(4-fluorophenyl)-1H-indole-3-yl]-1-butyl]-spiro[isobenzofuran-1(3H),4'-piperidine] or a pharmaceutically acceptable salt thereof may be administered in any suitable way e.g. orally or parenterally, and it may be presented in any suitable form for such administration, e.g. in the form of tablets, capsules, powders, syrups or solutions or dispersions for injection. Preferably, and in accordance with the purpose of the present invention, the compound of the invention is administered in the form of a solid pharmaceutical entity, suitably as a tablet or a capsule or in the form of a suspension, solution or dispersion for injection.

Methods for the preparation of solid pharmaceutical preparations are well known in the art. Tablets may thus be prepared by mixing the active ingredients with ordinary adjuvants and/or diluents and subsequently compressing the mixture in a convenient tableting machine. Examples of adjuvants or diluents comprise: corn, starch, lactose, talcum, magnesium stearate, gelatine, lactose, gums, and the like. Any other adjuvant or additive such as colourings, aroma, preservatives, etc. may also be used provided that they are compatible with the active ingredients.

The compound of the invention is most conveniently administered orally in unit dosage forms such as tablets or capsules, containing the active ingredient in an amount from about 10 $\mu$g/kg to 10 mg/kg body weight, preferably 25 $\mu$g/day/kg to 1.0 mg/day/kg, most preferably 0.1 mg/day/kg to 1.0 mg/day/kg body weight.

The fumarate of 1'-[4-[1-(4-fluorophenyl)-1H-indole-3-yl]-1-butyl]-spiro[isobenzo-furan-1(3H),4'-piperidine] can be prepared as described in Perregaard, J. et al., *J. Med. Chem.*, 1995, 38, 11, 1998–2008 (compound 14f) and the base and other pharmaceutically acceptable salts may be obtained therefrom by standard procedures.

Thus the acid addition salts according to the invention may be obtained by treatment of 1'-[4-[1-(4-fluorophenyl)-1H-indole-3-yl]-1-butyl]-spiro[isobenzo-furan-1(3H),4'-piperidine] with the acid in an inert solvent followed by precipitation, isolation and optionally re-crystallisation by known methods and if desired micronisation of the crystalline product by wet or dry milling or another convenient process, or preparation of particles from a solvent-emulsification process.

Precipitation of the salt is preferably carried out in an inert solvent, e.g. an inert polar solvent such as an alcohol (e.g. ethanol, 2-propanol and n-propanol).

Pharmacological Tests

The model of ultrasound-induced defence behaviour in the Lister hooded rats

The effect of the compound of the invention in the treatment of panic disorder was tested in the model of ultrasound-induced defence behaviour in the Lister hooded rats. This model which has been proposed by Beckett et al., 1996, supra, is based on the observation that rats exposed to an aversive stimulus like a predator emit ultrasonic vocalisations at a frequency between 18–27 kHz. These vocalisations have communicative value and convey the information of the aversive nature of the stimulus to other animals. The response of animals hearing the vocalisations consists of autonomic activation, analgesia and behavioural reflexes, which include freezing, flight and defensive aggression. This defensive state in the rat is considered to be analogous to panic attack in humans.

Playing artificially generated ultrasounds, in the 20 kHz frequency range, to naive rats influences their behaviour and they exhibit the defensive running associated with a panic attack. It has been shown that attenuation of the ultrasound-induced defensive behaviour was produced by agents which have anti-panic properties. Additionally, yohimbine, known as panic provocative agent induced potentiation of the ultrasound response (Beckett et al., 1996, supra). Cellular activation in the brain regions associated with the modulations of aversive responses has also been observed.

Experimental Procedure

The method has been previously described in detail (Beckett et al., 1996, supra). Briefly, male Lister hooded rats (Charles River, 250–300 g) were used. They were pretreated with drug (or vehicle) 30 min prior to the start of the test and placed in a circular open field testing arena (75 cm in diameter, 46 cm high walls) containing a piezo-electric speaker mounted above. After two minutes of baseline observation, the animals were exposed to a one minute 20 kHz square wave ultrasound tone (85 dB) followed by two minutes without sound. Ultrasound was produced using a multifunction signal generator. The animals' behaviour was monitored using an overhead video camera and subsequently analysed using a computer tracking system (Ethovision, Version 1.9, Noldus Information technology, The Netherlands). The behaviour of the animals was assessed as the total distance travelled during each two second period.

The average of all the baseline measures (30×2 s samples) was calculated thus giving a "baseline" score for each animal. This was used as a reference against which all the subsequent data points were compared. The baseline score was subtracted from the distance moved during each 2 s time bin from the minute in which the ultrasound was being played. This resulted in 30 values, some of which were positive and some of which were negative, all the positive values were added together giving a total score of the distance the animals ran above the baseline level, i.e. the amount of ultrasound-induced hyperactivity. Comparisons were made between the baseline levels of activity for the rats to exclude non-specific drug effects and between the ultrasound-induced increases in running.

Each experiment consisted of two control groups (each treated with vehicle), one of which was exposed to ultrasound and the other which was simply allowed to explore the arena for the full 5 min duration of the trial. In addition groups which were treated with drug were tested with exposure to the ultrasound stimulus.

Data were analysed using non-parametric analyses. Mann Whitney Rank sum tests for comparison of the two control groups (for the effect of the ultrasound) and analysis of variance on ranked data for comparison of the effects of drug on the ultrasound-induced response. ANOVA was followed by a post-hoc comparison (Mann Whitney rank sum test) where appropriate.

Results

The compound of the invention did not affect the baseline level of exploration of the animals indicating that the effect reported below was not due to non-specific effects of the compound of the invention on motor activity.

The control-USV animals demonstrated a significantly higher level of activity in the third minute (during which the ultrasound was being played) of the test than the non-ultrasound control animals ($P<0.01$ in both experiments. Mann Whitney rank Sum test).

The compound of the invention significantly reduced the defensive running at a dose of 0.63 mg/kg ($P<0.05$: Mann Whitney rank sum test).

Citalopram, a well known serotonic re-uptake inhibitor, was included in the tests for comparison purposes.

In view of the fact that the defensive running response is considered to be a model of panic attacks, the reduction in defensive running resulting form treatment with the compound of the invention is consistent with an anti-panic effect of this compounds.

What is claimed:

1. A method of treating a disease associated with panic attacks in a patient in need thereof, said method comprising administering the compound 1'-[4-[1-(4-fluorophenyl)-1H-indole-3yl]-1-butyl]-spiro[isobenzo-furan-1(3H),4'-piperidine], or a pharmaceutically acceptable salt thereof.

2. The method of claim 1, wherein said compound is administered in the form of the base or the fumarate.

3. The method of claim 1, wherein said compound is administered in the form of a unit dose.

4. The method of claim 3, wherein said unit dose comprises said compound in an amount from about 10 $\mu$g/kg to 10 mg/kg body weight.

5. The method of claim 3, wherein said unit dose comprises said compound in the amount of 25 $\mu$g/day/kg to 1.0 mg/day/kg.

6. The method of claim 5, wherein said unit dose comprises said compound in an amount from 0.1 mg/day/kg to 1.0 mg/day/kg body weight.

7. The method of claim 1 wherein said disease is selected from the group consisting of panic disorders, specific phobias, social phobia and agoraphobia.

8. The method of claim 7, wherein said disease is a specific phobia.

9. The method of claim 7, wherein said disease is social phobia.

10. The method of claim 7, wherein said disease is agoraphobia.

11. The method of claim 7, wherein said disease is panic disorder.

* * * * *